United States Patent [19]
Knowles, Jr. et al.

[11] Patent Number: 5,643,737
[45] Date of Patent: Jul. 1, 1997

[54] **MEROZOITE PROTEINS FOR USE IN DETECTION OF *BABESIA EQUI* IN HORSES USING IMMUNOLOGICAL TECHNIQUES**

[75] Inventors: Donald P. Knowles, Jr.; Lance E. Perryman, both of Pullman, Wash.

[73] Assignee: The United States of America as represented by the Secretary of Agriculture, Washington, D.C.

[21] Appl. No.: 400,413

[22] Filed: Mar. 2, 1995

Related U.S. Application Data

[63] Continuation of Ser. No. 902,164, Jun. 22, 1992, abandoned.

[51] Int. Cl.[6] .................. G01N 33/569; C07H 21/04; C07K 14/44; C07K 16/20
[52] U.S. Cl. .................. 435/7.22; 435/7.1; 435/7.92; 435/7.93; 435/342; 435/320.1; 435/252.3; 435/254.11; 435/7.2; 435/252.33; 435/7.95; 435/325; 436/811; 436/503; 436/536; 530/822; 530/350; 530/388.6; 530/389.5; 530/388.4; 530/809; 536/23.7
[58] Field of Search .................. 435/7.1, 7.22, 435/7.92, 7.93, 240.27, 240.2, 320.1, 252.3, 254.11, 7.2, 252.33, 7.95; 436/811, 503, 536; 536/23.7; 530/822, 350, 388.6, 389.5, 388.4, 809; 935/104, 108

[56] References Cited

U.S. PATENT DOCUMENTS 4,596,707  6/1986  Ristic et al. .................. 424/270.1
5,171,685  12/1992  McElwain et al. .................. 435/252.33

OTHER PUBLICATIONS

Seaver, Gen. Eng. News, 14: 10,21, 1994.

Knowles et al., J. Clin. Microbiol., 29: 2056–2058, 1991.

Nakamura et al., Chapter 27, from "Handbook of Exp. Imm., vol. 1: Immunochemistry" D. W. Weir ed, Blackwell Sci Press, 1986, pp. 27.1–27.20.

Knowles et al., Inf. and Imm., vol. 59, No. 7, 2412–17, 1991.

Posnett et al., *Molecular and Biochemical Parasitology*, vol. 34 (1989), pp. 75–78' "Repetitive DNA Probes for the Detection of *Babesia equi*".

*Primary Examiner*—Ronald B. Schwadron
*Attorney, Agent, or Firm*—M. Howard Silverstein; Joseph A. Lipovsky; John D. Fado

[57] ABSTRACT

The present invention relates to a purified and isolated merozoite protein which is a specific indicator of infection by *Babesia equi* (*B. equi*) in horses. This protein contains a conserved region found in all strains of *B. equi*. It has a molecular weight of approximately 28 KDa and has been successfully purified and sequenced. The isolated and purified merozoite protein is used to prepare antibodies which can then be used in a competitive inhibition enzyme linked immunosorbent assay for the diagnosis of *B. equi* infection in horses.

15 Claims, 7 Drawing Sheets

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 277 amino acids
        ( B ) TYPE: amino acid
        ( C ) STRANDEDNESS: double
        ( D ) TOPOLOGY: unknown     ( i i ) MOLECULE TYPE: cDNA     ( i i i ) HYPOTHETICAL: NO     ( i v ) ANTI-SENSE: NO     ( v i ) ORIGINAL SOURCE:
        ( A ) ORGANISM: Babesia equi
        ( B ) STRAIN: Florida
        ( D ) DEVELOPMENTAL STAGE: merozoite     ( v i i ) IMMEDIATE SOURCE:
        ( B ) CLONE: pEma1

( x i ) SEQUENCE DESCRIPTION: SEQ ID NO:1:

```
Arg  Pro  Pro  Val  Lys  Met  Ile  Ser  Lys  Ser  Phe  Ala  Phe  Val  Phe  Ala
 1              5                        10                          15

Ser  Ile  Ala  Ile  Ser  Ser  Ile  Leu  Ala  Glu  Glu  Glu  Lys  Pro  Lys  Ala
              20                        25                   30

Ser  Gly  Ala  Val  Val  Asp  Phe  Gln  Leu  Glu  Ser  Ile  Asp  His  Val  Thr
         35                        40                   45

Ile  Asp  Lys  Gln  Ser  Glu  Glu  His  Ile  Val  Tyr  Thr  Ala  His  Glu  Gly
    50                        55                   60

Tyr  Ala  Val  Glu  Lys  Val  Lys  Glu  Gly  Asp  Ser  Val  Ile  Lys  Thr  Phe
65                        70                   75                          80

Asp  Leu  Lys  Glu  Gln  Thr  Pro  Lys  Thr  Val  Val  Arg  His  Ile  Lys  Asp
                   85                        90                          95

Asn  Lys  Pro  Tyr  Val  Val  Ile  Ala  Val  Glu  Ser  Ala  Leu  His  Leu  Val
              100                       105                       110
```

-continued

| | | | | | | | | | | | | | | |
|---|---|---|---|---|---|---|---|---|---|---|---|---|---|---|
| Leu | Lys | Lys 115 | Asp | Gly | Asp | Lys | Trp 120 | Val | Glu | Leu | Glu | Val 125 | Ala | Glu | Phe |
| Tyr | Gln 130 | Glu | Val | Leu | Phe | Lys 135 | Gly | Phe | Glu | Ala | Val 140 | Ser | Val | Asp | Leu |
| Ala 145 | Ala | Ala | Val | Ser | Asp 150 | Lys | Phe | Thr | Glu | Thr 155 | Thr | Phe | Gly | Ser | Gly 160 |
| Lys | Lys | His | Thr | Phe 165 | Lys | Ala | Pro | Gly | Lys 170 | Arg | Val | Leu | Lys | Val 175 | Val |
| Asp | Gly | Lys | Thr 180 | Glu | Leu | Ile | Asp | Gly 185 | Asp | Asn | Glu | Val | Val 190 | Leu | Asp |
| Leu | Glu | Leu 195 | Phe | Val | Ser | Ser | Asp 200 | Asn | Lys | Val | Ala | Arg 205 | Val | Val | Tyr |
| Leu | Tyr 210 | Lys | Gly | Asp | Gly | Arg 215 | Ile | Lys | Glu | Ile | Phe 220 | Leu | Lys | Leu | Val |
| Glu 225 | Lys | Ala | Trp | Lys | Arg 230 | Val | Glu | Val | Lys | Asp 235 | Ala | Ala | Glu | Thr | Leu 240 |
| His | Gly | Ile | Asn | Ser 245 | Thr | Phe | Pro | Ala | Asp 250 | Tyr | Lys | Val | Val | Tyr 255 | Asp |
| Gly | Phe | Ser | Val 260 | Tyr | Gly | Ala | Leu | Leu 265 | Ala | Val | Ala | Ala | Ile 270 | Ala | Phe |
| Ser | Thr | Leu 275 | Phe | Tyr | | | | | | | | | | | |

MEROZOITE PROTEINS FOR USE IN DETECTION OF *BABESIA EQUI* IN HORSES USING IMMUNOLOGICAL TECHNIQUES

This application is a continuation of application Ser. No. 07/902,164, filed Jun. 22, 1992, now abandoned.

BACKGROUND OF THE INVENTION

1. Field of the Invention

The present invention relates to a purified and isolated merozoite protein derived by either conventional or recombinant means useful for the detection of *Babesia equi* in horses by means of a competitive inhibition enzyme-linked immunosorbent assay (CI ELISA). The instant invention likewise relates to antibodies to the protein as well as cell lines which produce the antibodies.

2. Description of the Related Art

Equine babesiosis, caused by *Babesia equi* or *Babesia caballi*, is a tick-borne hemoprotozoan disease of horses (Schein, E., 1988. *Equine Babesiosis*, pp. 197–208. In M. Ristic (Ed.), Babesiosis of Domestic Animals and Man. CRC Press, Boca Raton, Fla.). Clinical disease is characterized by fever, anemia, and icterus, most likely arising from hemolysis caused by merozoites, the intraerythrocytic stage of equine Babesia infection. Mortality rate is high during initial infection of horses introduced into enzootic regions, and horses which survive initial infection are protected from clinical disease upon subsequent challenge. It is hypothesized that this immunity acquired by horses in enzootic areas is the result of persistent infection.

The complement fixation test (CFT) is presently the official United States Department of Agriculture test for detecting antibody to *B. equi* and *B. caballi*. Horses with antibody to either parasite are restricted from importation into the United States. Three problems with the CFT are that (i) sera with anticomplement activity are not testable by the CFT; (ii) sera which react with CFT control erythrocyte antigen cannot be evaluated by the CFT; and (iii) sera containing specific immunoglobulin G(T) [IgG(T)] antibody may yield false-negative results because IgG(T) does not fix complement by the classical pathway.

Merozoite surface proteins are known to be important in the pathogenesis of hemoprotozoan diseases because of their role in parasite recognition of, attachment to, and penetration of host erythrocytes. Antigens recognized by antibody from hosts demonstrating immunity to clinical disease during Plasmodium spp., *B. rhodhaini*, *B. bovis*, and *B. bigemina* infection include surface proteins of merozoites, the only blood stage of the parasite that is extracellular and directly accessible to serum antibody. It has previously been demonstrated that cattle immune to infection with *B. bovis* had high-titered antibody preferentially directed against four immunodominant merozoite surface proteins (Hines et al., *Mol. Biochem. Parasitol.* 37:1–9; 1989). Invasion of erythrocytes by merozoites of *Plasmodium knowlesi* was inhibited by immune sera, and inhibition of *P. falciparum* merozoite invasion of erythrocytes in vitro required high concentrations of specific antibodies. These observations suggest that antibody to merozoite surface proteins may block erythrocyte invasion in vivo and that these proteins should be tested as potential immunogens.

Detection of antibodies has been the method of choice for diagnosis of infection with equine Babesia spp.; however, the specificity or role of antibodies in the acquired protective immunity against clinical disease following equine Babesia infection has not thus far been determined.

Applicants have now developed a competitive inhibition enzyme-linked immunosorbent assay (CI ELISA) based on the use of a merozoite protein for detection of antibody to *B. equi*. The formatting of the CI ELISA overcomes the above three problems related to use of the CFT. Furthermore, a high concordance was found to exist between the CI ELISA and CFT in detecting antibody to *B. equi*.

SUMMARY OF THE INVENTION

The present invention relates to the discovery and use of a novel merozoite protein of *Babesia equi* which has been isolated and purified. This protein contains a conserved epitope that is diagnostically useful as a sensitive and specific indicator of infection by Babesia equi in horses. The isolated protein has a molecular weight of approximately 28 kDa, with the amino acid sequence having been determined as follows:

| 1 | RPPVKMISKS | FAFVFASIAI | SSILAEEEKP | KASGAVVDFQ | LESIDHVTID |
|---|---|---|---|---|---|
| 51 | KQSEEHIVYT | AHEGYAVEKV | KEGDSVIKTF | DLKEQTPKTV | VRHIKDNKPY |
| 101 | VVIAVESALH | LVLKKDGDKW | VELEVAEFYQ | EVLFKGFEAV | SVDLAAAVSD |
| 151 | KFTETIFGSG | KKHTFKAPGK | RVLKVVDGKT | ELIDGDNEVV | LDLELFVSSD |
| 201 | NKVARVVYLY | KGDGRIKEIF | LKLVEKAWKR | VEVKDAAETL | HGINSTFPAD |
| 251 | YKVVYDGFSV | YGALLAVAAI | AFSTLFY 277 | | |

The isolated and purified merozoite protein is used to prepare antibodies which are useful in immunoassays for the diagnosis of *B. equi* in horses. A molecular clone of the protein expressing the conserved epitope has been obtained and shown to likewise be useful in such immunoassays. This recombinant merozoite protein is designated SEQ ID NO:1.

It is an object of this invention to provide an immunological assay for *B. equi* in horses based upon the antigenicity of a conserved epitope of a novel merozoite protein of It is also an object of this invention to provide hybridomas for the production of antibodies to the conserved epitope of the merozoite protein.

It is a further object of this invention to provide antibodies as immunochemical reagents for the diagnosis of *B. equi* in horses.

Other objects and advantages of this invention will become readily apparent from the ensuing description.

DETAILED DESCRIPTION OF THE INVENTION

In the present invention a novel protein isolated and purified from the merozoite of *B. equi* has been discovered and proven to be a sensitive and specific indication of the presence of antibodies to *B. equi* in horses. The novel protein of the invention is effective for use in immunoassays such as the competitive inhibition enzyme-linked immunosorbent assay (CI ELISA). Samples used in the test may be obtained from the serum of the horse to be tested. Immunoprecipitation of *B. equi* merozoite proteins recovered from an infected horse were found to have apparent molecular masses of 210, 144, 108, 88, 70, 56, 44, 36, 34, 28 and 25 kDa. The descri 36/133.97 was found to react with a protein epitope on the 44-, 36-, 34-, and 28-kDa merozoite antigens. This monoclonal antibody, 36/133.97, has been deposited under the Budapest Treaty in the American Type Culture Collection (12301 Parklawn Drive, Rockville, Md., 20852, USA) on Jan. 10, 1995, and has been assigned Deposit Number ATCC HB11788. Applicants found, through a competitive binding assay, that horses infected with *B. equi* throughout the world consistently produce antibodies to the antigens associated with this epitope. The 28-kDa antigen was found to be of particular interest due to its immunodominance in infected horses as recognized by MAb 36/133.97 in serum dilution studies. This protein was subsequently determined to possess the amino acid sequence:

| 1   | RPPVKMISKS | FAFVFASIAI | SSILAEEEKP | KASGAVVDFQ | LESIDHVTID |
|-----|------------|------------|------------|------------|------------|
| 51  | KQSEEHIVYT | AHEGYAVEKV | KEGDSVIKTF | DLKEQTPKTV | VRHIKDNKPY |
| 101 | VVIAVESALH | LVLKKDGDKW | VELEVAEFYQ | EVLFKGFEAV | SVDLAAAVSD |
| 151 | KFTETTFGSG | KKHTFKAPGK | RVLKVVDGKT | ELIDGDNEVV | LDLELFVSSD |
| 201 | NKVARVVYLY | KGDGRIKEIF | LKLVEKAWKR | VEVKDAAETL | HGINSTFPAD |
| 251 | YKVVYDGFSV | YGALLAVAAI | AFSTLFY 277 |            |            | hereby designated as SEQ ID NO:1.

The mRNA associated with the 28 kDa merozoite protein of *B. equi*, as isolated in Example II, may be used as a template in the synthesis of cDNA by conventional techniques such as those described by Maniatis (1982, Molecular Cloning: A Laboratory Manual. Cold Spring Harbor Laboratory, Cold Spring Harbor, N.Y.), herein incorporated by reference.

The selected vector may be cut with an appropriate restriction enzyme, ligated via conventional techniques to the ends of the fragments of *B. equi* cDNA, and inserted into a host microorganism resulting in the synthesis of the 28 kDa protein referred to hereinabove. Without being limited thereto, suitable techniques for the preparation of vectors and transformed microorganisms are described by Drummond et al., U.S. Pat. No. 5,041,378, issued Aug. 20, 1991; the contents of which are herein incorporated by reference.

The antigen may be employed for the generation of hybrid cell lines producing MAb's specific thereto. Establishing the antibody-secreting cell lines for use in the invention is a multistep procedure which includes hyperimmunizing an animal to induce a proliferation of antibody-producing cells, promoting fusion between the primed cells and cells of an immortal cell line, selecting for antibody-secreting hybridomas, screening the hybridomas for selectability in a subsequent fusion stage, and then cloning the antibody producing hybrids. The practitioner skilled in the art would recognize that hybrid cell lines could be produced by conventional techniques. Suitable techniques for the generation of hybrid cell lines include those described by Kohler and Milstein (*Nature;* Vol. 256; pp. 495–497; 1975); herein incorporated by reference; and Stites (*Clinical Laboratory Methods for Detection of Antigens and Antibodies. In Basic and Clinical Immunology;* Stites et al. (Ed.) Lang Medical Publications, Los Altos, Calif., 1984, pp. 350–351). Without being limited thereto, particularly preferred is, the hybrid cell line producing MAb 36/133.97 discussed in Example IV below. The resultant MAb produced from the cell line binds selectively with *B. equi*.

It is envisioned that the monoclonal antibody (MAb) specific for the 28 kDa merozoite protein of this invention may be employed for the detection of infection by *B. equi* in clinical specimens, particularly serum, by use of conventional immunoassay techniques. Such an immunoassay would comprise the steps of: A) collecting serum from a horse to be tested; B) contacting the serum with antibodies specific for a conserved epitope of a merozoite protein of *B. equi;* and C) detecting the presence of the antigen-antibody complex. While the skilled practitioner will recognize that suitable immunoassay techniques include IFA, immunoelectrophoresis and Western Blot; enzyme-linked immunosorbent assays (ELISA) are preferred, with competitive inhibition enzyme-linked immunosorbent assays (CI ELISA) as described in Knowles et al. (*Infect. Immun.* 59:2412–2417, 1991), herein incorporated by reference, being most preferred.

The present invention is not limited to any specific separation or identification methodology. Rather, all modifications obvious to one skilled in the art are envisioned and encompassed by the present invention. The following examples are offered to illustrate the present invention and are not intended to limit its scope.

EXAMPLE I

*Babesia equi* isolates

A *B. equi* isolate was obtained in 1976 from a horse in Florida and cryopreserved as a blood stabilate containing 10% dimethyl sulfoxide in liquid nitrogen. A nonsplenectomized horse (H5) was infected with 30 ml of the Florida *B. equi* first-passage stabilate containing $5.6\times10^6$ viable organisms per ml. Viability was determined by incubating merozoites with fluorescein diacetate (FDA) as described by Rotman et al. (*Proc. Natl. Acad. Sci.* USA 55:134–141; 1966). This horse was monitored for clinical disease and parasitemia. During ascending parasitemia, 200 ml of whole blood was passaged to a splenectomized horse. At peak parasitemia (49%), infected erythrocytes were collected and stored in liquid nitrogen as a blood stabilate containing packed erythrocytes 1:1 with a cryopreservant of 20% (wt/vol) polyvinylpyrrolidone and 2% (wt/vol) glucose in Puck's saline G (GIBCO Laboratories, Chagrin Falls, Ohio); see Palmer et al. (*Parasitology* 84:567–572; 1982). Aliquots (25 ml) of washed packed infected erythrocytes were frozen at −70° C.

The Europe isolate of *B. equi* was obtained from a mare from Georgia, USSR; gee Kutler et al. (Am. J. Vet. Res. 47:1668–1670; 1986). A splenectomized pony was infected with the Europe isolate, and blood smears for indirect immunofluorescence assay (IFA) were prepared.

EXAMPLE II

In vitro translation of *B. equi* mRNA

*B. equi* merozoite mRNA was isolated from infected erythrocytes by modification of methods previously described by Maniatis et al. (*Molecular Cloning: A Laboratory Manual.* Cold Spring Harbor Laboratory, Cold Spring Harbor, N.Y.; 1982). A 25 ml aliquot of washed packed infected erythrocytes was thawed in the presence of equal volumes of guanidinium isothiocyanate (4.0 M guanidinium isothiocyanate [Bethesda Research Laboratories, Gaithersburg, Md.], 0.1 M Tris-HCl [pH 7.5], 1% 2-mercaptoethanol, 2% SARKOSYL® (N-Lauroylsarcosine, sodium salt) 0.01 M EDTA [pH 7.6]). Lysates were sequentially extracted with buffered phenol, phenol-chloroform-isoamyl alcohol, and ether before nucleic acids were ethanol precipitated. Polyadenylated mRNA was isolated by POLY(U)SEPHADEX® (Bethesda Research Laboratories) chromatography. In parallel, mRNA was isolated from 25 ml of washed packed uninfected erythrocytes. Stained smears of washed infected erythrocytes revealed less than 1 leukocyte per $10^4$ erythrocytes. Integrity of mRNA was evaluated by the migration of rRNA species in 1% agarose gel. Merozoite mRNA was translated in vitro (Promega, Madison, Wis.), using 2 μg of polyadenylated mRNA per reaction and a nuclease-treated rabbit reticulocyte lysate; see Jackson et al. (*Methods Enzymol.* 96:50–71; 1983) and Pelham et al. (*Eur. J. Biochem.* 67:247–256; 1976). The rabbit reticulocyte lysate was chosen because it lacks microsomal membranes necessary for processing events such as signal peptide cleavage and core glycosylation.

EXAMPLE III

Radiolabeling of *B. equi* proteins

Defibrinated blood from a splenectomized horse infected with the Florida isolate of *B. equi* was collected when ascending parasitemia reached 5%. Erythrocytes were washed twice in Puck's saline G to remove the majority of buffy coat cells. A final wash was made in serum- and amino acid-free medium 199 (Hazleton Laboratories, Lenexa, Kans.). Short-term cultures were established in 2.5-$cm^2$ flasks at a 10% erythrocyte suspension in amino acid-free medium 199 containing 40% autologous, preinoculation horse serum, 1% penicillin G, streptomycin, amphotericin B, 25 μCi (500 μCi total) each of tritiated isoleucine, lysine, tyrosine, valine, and arginine per ml (respective specific activities, 110.8, 97.4, 46.7, 64.6, and 53.3 Ci/mmol; Dupont-New England Nuclear, Boston, Mass.) and buffered with 10 mM 3-[N-tris-(hydroxymethyl)methylamino]-2-hydroxy propanesulfonic acid, pH 7.35. Metabolic labeling proceeded during an 18-h incubation period at 37° C. in 5% $CO_2$ and ambient air. The labeled cells were then washed and solubilized as described by McElwain et al. (*J. Immunol.* 138:2298–2304; 1987). In vitro translation products were labeled with $[^{35}S]$ methionine at 0.8 mCi/ml per reaction.

EXAMPLE IV

Production of monoclonal antibody (Mab)

Eight-week-old BALB/c mice were immunized subcutaneously with $10^7$ viable merozoites in 0.1 ml of phosphate-buffered saline (PBS) emulsified in an equal volume of Freund's complete adjuvant. Merozoites for MAb production were prepared from stabilates containing a 49% parasitemia. The stabilates were diluted with 2 volumes of PBS and centrifuged at 2,500×g for 5 min. Pellets were lysed for 30 s with an equal volume of distilled water, diluted with 3 ml of PBS, vortexed gently, and centrifuged at 400×g for 5 min. The supernatant was centrifuged at 2,500×g to pellet the merozoites. Two additional immunizations consisting of the same number of parasites in incomplete Freund's adjuvant were given subcutaneously at 10-day intervals. The mice were then immunized intravenously with $10^7$ viable merozoites in 0.1 ml of PBS 72 h prior to fusion. Cell fusions and cloning by limiting dilution were performed utilizing x63-A68.653 murine myeloma cells utilizing methods described by Riggs et al. (*J. Immunol.* 143:1340–1345; 1989). The CI ELISA used an IgG1 MAb (36/133.97) which reacts with a protein epitope on the surface of *B. equi* merozoites as disclosed by Knowles et al. (*Infect. Immun.* 59:2412–2417; 1991). Heavy-chain isotypes were identified by enzyme-linked immunosorbent assay (ELISA), and concentrations of antibodies were determined by immunodiffusion; as described by Johnstone et al. (1982, *Precipitation*

*Techniques in Agar and Agarose*, pp. 120–140. In A. Johnstone and R. Thorpe (Ed.), Immunochemistry in Practice. Blackwell Scientific Publications, Boston). Supernatants from the initial fusion and from limiting-dilution clones were screened by IFA with acetone-fixed *B. equi* organisms.

EXAMPLE V

Immune sera from horses experimentally and naturally infected with *B. equi*

Serum was obtained from an adult horse (H5) infected intravenously twice at a 2-month interval with a Florida isolate of *B. equi*. After 50 ml of serum was obtained, the initial inoculation of H5 was with 30 ml of a first-passage stabilate of a Florida isolate of *B. equi*. This stabilate in 10% dimethyl sulfoxide contained $5.6 \times 10^6$ viable merozoites per ml. The second inoculation was with a 2.0-ml stabilate containing a 49% parasitemia prepared as described for *B. equi* isolates. Equine sera that tested positive for antibodies to *B. equi* by the complement fixation test; see Hirato et al. (*Jpn. J. Vet. Sci.* 7:197–205; 1945) were obtained from the National Veterinary Services Laboratory, U.S. Department of Agriculture, Ames, Iowa. These sera were obtained from horses in 19 countries, the data regarding such are herein presented as Table 1.

TABLE I

CI ELISA for assessment of antibodies to *B. equi* merozoite proteins recognized by MAb 36/133.97

| Country of origin | OD at serum dilution of [a]: | | | | CI titer[b] |
|---|---|---|---|---|---|
| | $10^{-1}$ | $10^{-2}$ | $10^{-3}$ | $10^{-4}$ | |
| Argentina | 0.252 | 0.483 | 1.130 | 1.027 | $10^{-2}$ |
| Austria | 0.563 | 0.703 | 0.826 | 0.948 | $10^{-2}$ |
| Brazil | 0.126 | 0.236 | 0.641 | 0.824 | $10^{-3}$ |
| Chile | 0.650 | 0.866 | 1.241 | 1.315 | $10^{-1}$ |
| Colombia | 0.180 | 0.713 | 1.259 | 1.191 | $10^{-2}$ |
| Ecuador | 0.247 | 0.543 | 1.055 | 1.263 | $10^{-2}$ |
| England | 0.292 | 0.816 | 1.233 | 1.237 | $10^{-1}$ |
| France | 0.238 | 0.608 | 1.110 | 1.229 | $10^{-2}$ |
| Italy | 0.378 | 0.804 | 1.181 | 1.292 | $10^{-1}$ |
| Netherlands | 0.148 | 0.266 | 0.740 | 1.093 | $10^{-2}$ |
| North Yemen | 0.663 | 0.851 | 1.166 | 1.193 | $10^{-1}$ |
| Panama | 0.240 | 0.484 | 1.066 | 1.139 | $10^{-2}$ |
| Peru | 0.185 | 0.540 | 1.012 | 1.077 | $10^{-2}$ |
| Poland | 0.601 | 1.000 | 1.247 | 1.185 | $10^{-1}$ |
| Saudi Arabia | 0.420 | 0.771 | 1.218 | 1.266 | $10^{-1}$ |
| Spain | 0.295 | 0.607 | 0.687 | 0.733 | $10^{-3}$ |
| Trinidad | 0.269 | 0.594 | 1.143 | 1.227 | $10^{-2}$ |
| United States | 0.202 | 0.377 | 1.012 | 1.264 | $10^{-2}$ |
| Venezuela | 0.325 | 0.771 | 1.244 | 1.324 | $10^{-1}$ |

[a]OD of MAb 36/133.97 reaction with *B. equi* merozoites with equine serum at the specified dilution. OD for isotype control MAb with *B. equi* merozoites = $0.153 \pm 0.05$ (n = 8).
[b]Dilution of serum reducing OD values to less than 3 standard deviations below the mean for control horses (<0.73) in CI ELISA with MAb 36/133.97. OD for control horses at a ½ dilution = $0.97 \pm 0.08$ (n = 68). Controls included preinoculation sera of H5 and SN76N8401 (control serum from the National Veterinary Services Laboratory, Ames, Iowa).

EXAMPLE VI

Immunoprecipitation and SDS-PAGE

Immunoprecipitation of radiolabeled antigen was performed as previously described by McElwain et al. (*J. Immunol.* 138:2298–2304; 1987). A total of $1 \times 10^6$ to $2 \times 10^6$ trichloroacetic acid-precipitable counts of antigen and 10 µg of MAb or 10 µl of equine immune serum were used in each precipitation. Immune complexes were precipitated with protein A (Pansorbin; Calbiochem, San Diego, Calif.) or protein G (Immu-Bind; Genex, Gaithersburg, Md.). Metabolically radiolabeled antigen, in vitro-translated proteins, or immunoprecipitates were boiled for 3 min in sodium dodecyl sulfate (SDS)-polyacrylamide gel electrophoresis (PAGE) sample buffer (final concentrations of 25 mM Trio [pH 6.8], 2% [wt/vol] SDS, 15% [vol/vol] glycerol, 2.5% 2-mercaptoethanol, and a few crystals of bromophenol blue) and were electrophoresed in a 7.5 to 17.5% SDS-polyacrylamide gradient slab gel with a 5% stacking gel; (see Takacs, B. 1979. *Blectrophoresis of Proteins in Polyacrylamide Slab Gels*, pp. 81–105. In I. Lefkovits and B. Pernis (Ed.), *Immunological Methods*. Academic Press, Inc., N.Y.). SDS-polyacrylamide gels were processed for autoradiography as described previously. 14C-labeled standards used for molecular weight comparisons (Amersham, Arlington Heights, Ill.) consisted of myosin (200,000), phosphorylase b (92,500), bovine serum albumin (69,000), ovalbumin (46,000), carbonic anhydrase (30,000), and lysozyme (14,300).

EXAMPLE VII

Western immunoblotting

Western blotting was performed on a miniblotter 25 (Immunetics, Cambridge, Mass.) by modification of the techniques of Towbin et al. (*J. Immunol.* Methods 72:313–340). Merozoite antigen was prepared from stabilates containing a 49% parasitemia as described for MAb production. Control erythrocyte antigen was prepared identically to merozoite antigen and was obtained from stabilates prepared from an uninfected horse. Pelleted merozoites were added to equal volumes of SDS-PAGE sample buffer and boiled for 10 min. Merozoite proteins separated in SDS-PAGE (as previously described) were electrophoretically transferred overnight to nitrocellulose filters in 25 mM Tris-190 mM glycine buffer containing 20% (vol/vol) methanol. Filters were blocked for 2 h in 0.17 M NaCl-0.01 M Trts-0.1 mM phenylmethylsulfonyl fluoride-1.0% (wt/vol) bovine hemoglobin (buffer A). Serum (50 µl) or MAb (10 µg) was diluted in buffer A with the addition of 0.1% (wt/vol) SDS-0.1% (vol/vol) TRITON X-100®-(polyethylene glycol p-isooctylphenyl ether) 1.0 mM EDTA (buffer B). Bound antibodies were detected by incubation for 1 h each in second antibody (rabbit anti-horse or rabbit anti-murine immunoglobulin) and $^{125}$I-protein A in buffer B. Filters were washed three times in buffer B after incubation with equine serum or MAb, second antibody, and $^{125}$I-protein A, followed by three washes in buffer B without hemoglobin before drying and autoradiography. $^{14}$C-labeled molecular weight standards were the same as for SDS-PAGE previously described.

EXAMPLE VIII

IFA (i) Fixed *B. equi*

IFA of acetone-fixed *B. equi* was performed as described previously by McGuire et al. (*Infect. Immun.* 45:697–700; 1984). Bound murine or equine antibodies were detected with fluorescein isothiocyanate-conjugated rabbit anti-mouse immunoglobulin or goat anti-horse immunoglobulin.

(ii) Live *B. equi*

Merozoites for live IFA were prepared from stabilates containing a 49% parasitemia as described for MAb production. Live IFA was performed by minor modification of methodology previously described by Goff et al. (*Infect. Immun.* 56:2363–2368; 1988). Merozoite pellets resuspended in 100 μl of PBS were incubated with 25 μg of MAb 36/133.97. After a 30-min incubation at room temperature, the cells were washed three times with 10% normal goat serum in PBS, diluted to 975 μl with normal goat serum-PBS, and added to 12.5 μg of goat anti-mouse antibody conjugated with tetramethylrhodamine isothiocyanate (Kirkegaard & Perry Laboratories, Gaithersburg, Md.). Samples were incubated for 30 min, washed three times with PBS, and mixed with 2.0 μl of a 5-mg/ml solution of FDA. Samples were incubated for 15 min, washed once with PBS, resuspended in 100 μl of PBS, and examined in a wet mount by phase and fluorescence microscopy. A total of 757 FDA-positive merozoites were examined for reactivity to MAb 36/133.97.

EXAMPLE IX

CI ELISA

A competitive inhibition (CI) ELISA was established to test for a direct relationship between proteins recognized by immune equine sera and MAb 36/133.97. Merozoites were prepared as described for MAb production. Merozoite preparations were diluted to 40 μg/μl in PBS containing 20 mM MgCl$_2$ and treated with an equal volume of lysis buffer (50 mM Tris [pH 8.0], 5 mM EDTA, 5 mM iodoacetamide, 0.1 mM N-Cα-p-tosyl-L-lysine chloromethyl ketone, and 1.0 mM phenylmethylsulfonyl fluoride in 1.0% NONDET-P-40®). (octylphenol-ethylene oxide condensate containing an average of nine moles ethylene oxide per mole of phenol) Lysates were placed on ice for 15 min and then centrifuged at 1,500×g for 15 min, and the supernatant was collected. Four microliters of supernatant adjusted to 0.20 μg of protein per μl was added to individual wells of IMMULON-2® (96 well, non-reactive plastic flat-bottom plates (Dynatech Laboratories, Chantlily, Va.) and incubated overnight at room temperature. Each well was blocked for 2-h with 350 μl of 20% milk in PBS containing 0.2% TWEEN 20® (polyoxyethylenesorbitan monolaurate) (buffer A). Equine sera were diluted in buffer A to a final volume of 290 μl and added to the wells. Samples were incubated for 30 min, 0.125 μg of MAb 36/133.97 in 10 μl of buffer A was added, and the reaction mixture was incubated for 1-h at room temperature. Wells were washed three times with PBS containing 0.2% TWEEN 20 (buffer B). Biotinylated equine anti-murine immunoglobulin G (IgG; Vector Laboratories, Burlingame, Calif.) in buffer A was added, incubation was continued for 30 min, and the wells were washed three times with buffer B. Addition of avidin-conjugated alkaline phosphatase (Vector Laboratories) in buffer B was followed by a 30-min incubation. Wells were washed three times with buffer B, and 100 μl of a 1.0-g/μl solution of p-nitrophenyl phosphate in 100 mM NaHCO$_3$ (pH 9.5) with 10 mM MgCl$_2$ (Sigma Laboratories, St. Louis, Mo. ) was added to each well. Following a 30-min incubation, reactions were stopped with 50 μl of 0.2 M EDTA and the optical density (OD) was read at 405 nm on a Dynatech MR-5000 ELISA plate reader.

EXAMPLE X

Immunoprecipitation of *B. equi* merozoite proteins with equine serum

Figure 1:
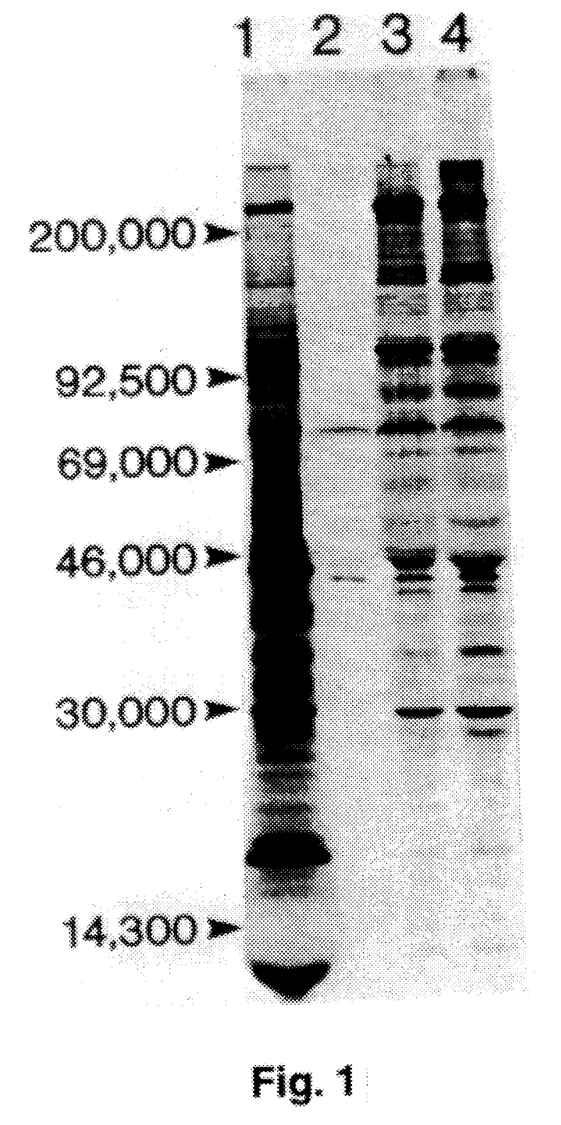
FIG. 1. Immunoprecipitation of ³H-amino acid-labeled merozoite-associated proteins of *B. equi* with serum from experimentally infected horse H5. Shown are labeled protein profile (lane 1), preinoculation serum (lane 2), postinoculation serum (2 months after primary infection) (lane 3), and post-second inoculation serum (1 month after second infection; 3 months after primary infection) (lane 4).

FIG. 1 shows immunoprecipitation of *B. equi* merozoite proteins with pre- and postinoculation serum from horse H5 infected with a Florida isolate of *B. equi*. The major *B. equi* merozoite proteins recognized by antibodies from this horse have apparent molecular masses of 210, 144, 108, 88, 70, 56, 44, 36, 34, 28, and 25 kDa. Immunoprecipitations with sera from 10 additional experimentally infected and 2 naturally infected horses provided similar results.

EXAMPLE XI

Immunoprecipitation of *B. equi* antigens with MAb 36/133.97

Figure 2:
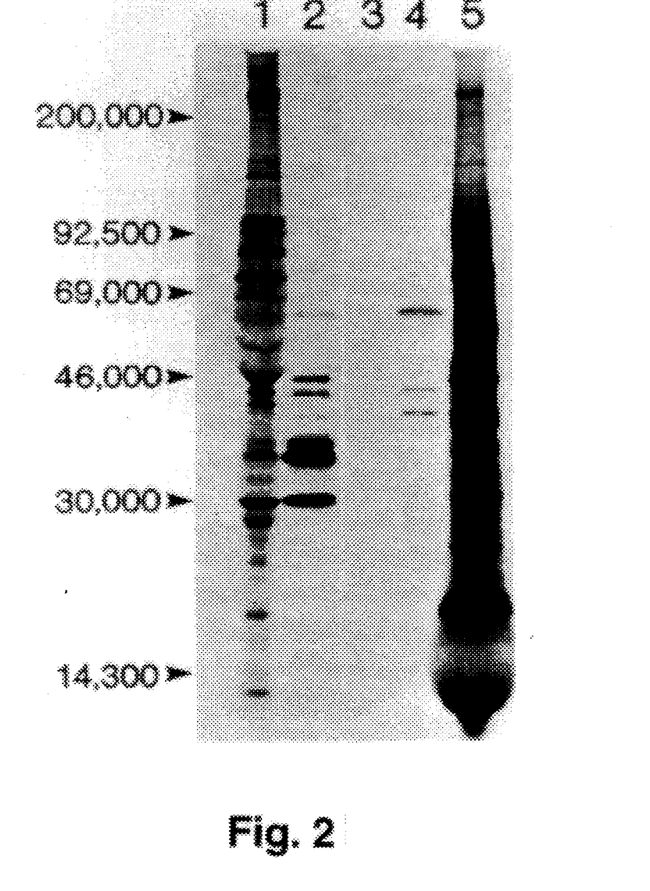
FIG. 2. Immunoprecipitation of ³H-amino acid-labeled merozoite-associated proteins of *B. equi* with MAb 36/133.97. Shown are postinfection serum, horse H5 (lane 1), MAb 36/133.97 (lane 2), MAb isotype control (lane 3), protein A control (lane 4), and labeled protein profile (lane 5).

An autoradiograph comparing immunoprecipitation of merozoite proteins with MAb 36/133.97 and equine immune serum is shown in FIG. 2. MAb 36/133.97, isotyped as IgG1, immunoprecipitated proteins with approximate molecular masses of 44, 36, 34, and 28 kDa which comigrated with proteins immunoprecipitated by serum from infected horse H5.

EXAMPLE XII

IFA of fixed and live merozoites with MAb 36/133.97

The epitope recognized by MAb 36/133.97 is conserved on at least two isolates of *B. equi*, as determined by reactivity in IFA. MAb 36/133.97 reacted with both the Florida and Europe; see Kutler et al. (*Am. J. Vet. Res.* 47:1668–1670, 1986), isolates of *B. equi* at a final concentration of 0.66 μg/ml. Up to 100% of merozoites from the Florida and Europe isolates of *B. equi* reacted with MAb 36/133.97 in fixed IFA. MAb 36/133.97 did not react with uninfected erythrocytes or *B. caballi* in IFA. At the same concentrations, IgG1 isotype control MAb and rabbit anti-mouse second antibody did not react with *B. equi*-infected erythrocytes. The surface reactivity of MAb 36/133.97 was demonstrated by its binding to viable (FDA-positive) merozoites. Approximately 80% of isolated merozoites stained with FDA and 64% (482 of 757) of FDA-positive merozoites reacted diffusely with MAb 36/133.97.

EXAMPLE XIII

Protein character of the epitope and immunodominance of the protein recognized by MAb 36/133.97

Figure 3A:
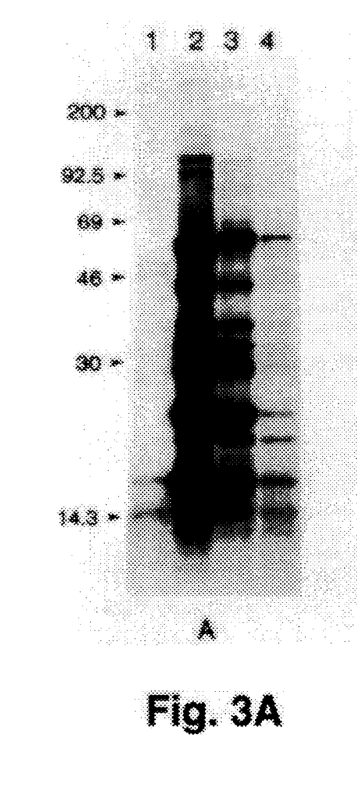
FIG. 3A. Comparisons of immunoprecipitations of [$^{35}$S] methio-nine-labeled in vitro translation products with dilutions of sera from experimentally infected horse H5. $10^{-2}$ dilution of H5 preinoculation serum (lane 1), $10^{-2}$ dilution of H5 postinoculation serum (lane 2), $10^{-3}$ dilution of H5 postinoculation serum (lane 3), $10^{-4}$ dilution of H5 postinoculation serum (lane 4).
Figure 3B:
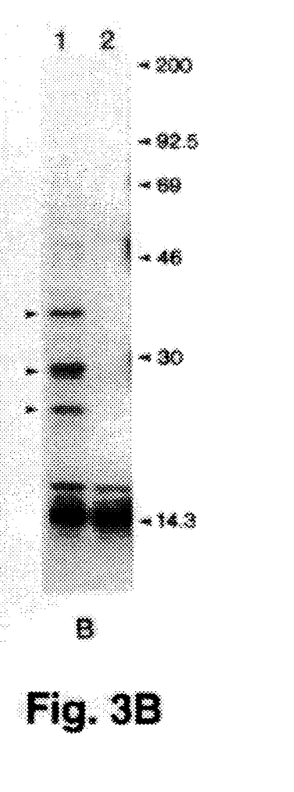
FIG. 3B. Comparisons of immunoprecipitations of [$^{35}$S] methio-nine-labeled in vitro translation products with dilutions of sera from MAb 36/133.97 (lane 1) and MAb isotype control (lane 2). Arrowheads indicate locations of 38-,28-, to 26-, and 23-kDa proteins.

Equal volumes of washed packed erythrocytes from infected and uninfected horses yielded 5.7 and 0.22 μg of polyadenylated RNA. The small amounts of polyadenylated RNA isolated from uninfected erythrocytes provided insufficient incorporation of [$^{35}$S]methionine from in vitro translation for use in immunoprecipitations. Immunoprecipitation of in vitro-translated *B. equi* mRNA with serum from infected horse H5 and with MAb 36/133.97 is shown in FIG. 3A and 3B. MAb 36/133.97 immunoprecipitated proteins at 38, 28, 26, and 23 kDa (FIG. 3B, arrowheads) which comigrated with proteins immunoprecipitated by serum from horse H5 at $10^{-3}$ to $10^{-4}$ dilutions (FIG. 3A). In vitro translation products derived from rabbit reticulocyte lysate are not glycosylated. Therefore, immunoprecipitation of these products by MAb 36/133.97 indicates that the binding site recognized by this antibody is a protein epitope. Immunoprecipitation of in vitro-translated *B. equi* mRNA with sera from four naturally infected horses provided similar results.

Figure 4:
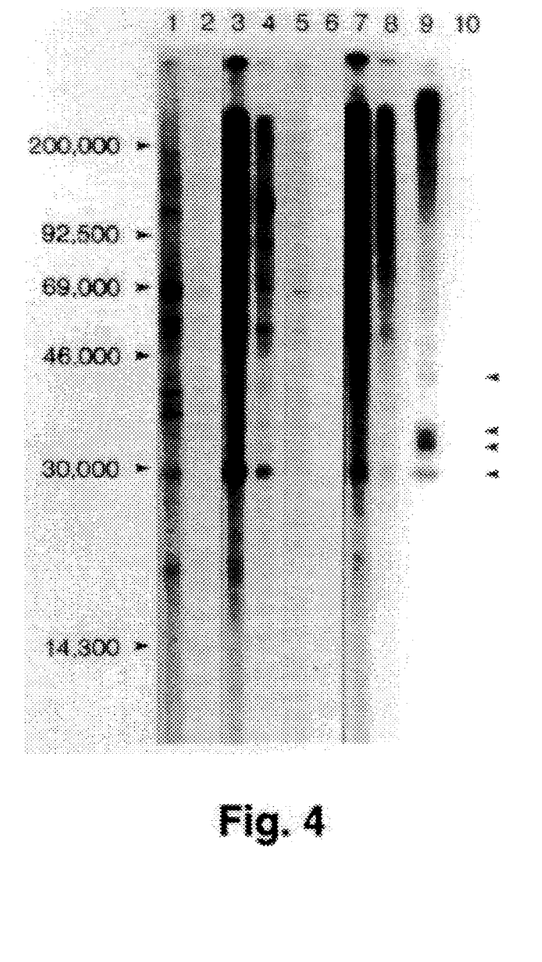
FIG. 4. Comparisons of dilutions of sera from infected horses and MAb 36/133.97 in Western blots: H5 preinoculation serum, $10^{-3}$ (lane 1) and $10^{-4}$ (lane 2); H5 postinoculation serum, $10^{3}$ (lane 3) and $10^{-4}$ (lane 4); SN76N8401 (control serum from the National Veterinary Services Laboratory, Ames, Iowa), $10^{-3}$ (lane 5) and $10^{-4}$ (lane 6); naturally infected horse serum, $10^{-3}$ (lane 7) and $10^{-4}$ (lane 8); MAb 36/133.97 (lane 9); and MAb isotype control (lane 10). Arrowheads indicate locations of 44-, 36-, 34-, and 28-kDa proteins.

In Western blot analysis, MAb 36/133.97 did not react with antigen from uninfected erythrocytes; however, it recognized proteins of 44, 36, 34, and 28 kDa prepared from stabilates of infected erythrocytes (FIG. 4, arrowheads). Evaluation of diluted horse sera demonstrated reactivity with a 28-kDa protein at a dilution of $10^{-4}$ as also seen in FIG. 4.

EXAMPLE XIV

Relatedness of proteins recognized by sera from *B. equi* infected horses and MAb 36/133,97

Relatedness of proteins recognized by MAb 36/133.97 and sera *B. equi*-infected horses was investigated by a CI ELISA. Sera from 34 noninfected horses allowed MAb 36/133.97 to bind in the CI ELISA with OD values of 0.97±0.08. Thus, inhibition of MAb binding to *B. equi* merozoites was considered significant at OD values of <0.73, corresponding to mean OD minus 3 standard deviations. Table I shows that sera from infected horses from 19 countries significantly inhibited the binding of MAb 36/133.97 to isolated merozoites. At a $10^{-1}$ dilution, sera from all infected horses uniformly inhibited binding in the CI ELISA. Some of these sera also inhibited the binding of MAb 36/133.97 at dilutions of $10^{-2}$ and $10^{-3}$.

EXAMPLE XV

One hundred fifty-four equine serum samples from 19 countries in North America (6 samples), South America (113 samples), Europe (28 samples), and the Middle East (7 samples) were obtained from the National Veterinary Services Laboratory, USDA-APHIS, Ames, Iowa. Each serum was tested for antibody to *B. equi* by the CFT as described by Frerichs et al. (*Am. J. Vet. Res.* 30:697–702, 1337–1341; 1969). Three anticomplement serum samples and one serum sample reactive with the CFT erythrocyte antigen control were also obtained from the National Veterinary Services Laboratory. H5 serum is from a horse experimentally infected with stabilate of a Florida *B. equi* isolate as disclosed by Knowles et al. (*Infect. Immun.* 59:2412–2417; 1991) and SN76N8401 is a GFT-negative control serum obtained from the National Veterinary Services Laboratory. One hundred and four equine serum samples submitted to Washington State University for equine infections anemia testing were used as control sera.

A CI ELISA was performed on all samples utilizing applicants' recombinant antigen preparation of Example in conjunction with the protocol set forth in Example IX. Serum samples were tested by CI ELISA in groups of 5 to 15 per day without knowledge of the CFT results. Duplicates of each serum sample were tested at dilutions of 1:2 and 1:10. Five to 10 different control serum samples were tested at a 1:2 dilution in duplicate each day. A mean and standard deviation of the OD for the control serum samples was calculated following each test day. A serum sample was considered positive for antibody to *B. equi* if it inhibited the binding of MAb 36/133.97 such that the mean duplicate OD value for that dilution of test serum as at least 3 standard deviations below the mean OD value of the control serum samples for that test day. Sample data from the CI ELISA and CFT for a test day are given in Table 2.

TABLE II

Sample data from CI ELISA and CFT[a]

| | CI ELISA, OD[b] | | CFT titer[c] | |
|---|---|---|---|---|
| Serum | 1:2 | 1:10 | *B. equi* | *B. caballi* |
| 224 | 0.381, 0.389 | 0.382, 0.441 | 1:5 | 1:40 |
| 225 | 0.471, 0.486 | 0.732, 0.721 | 1:5 | Negative |
| 226 | 1.489, 1.470 | 1.717, 1.672 | Negative | 1:5 |
| 227 | 1.337, 1.369 | 1.146, 1.619 | Negative | 1:40 |
| 228 | 0.217, 0.156 | 0.229, 0.236 | 1:40 | 1:20 |
| 229 | 0.301, 0.298 | 0.336, 0.363 | 1:5 | 1:40 |

TABLE II-continued

Sample data from CI ELISA and CFT[a]

| | CI ELISA, OD[b] | | CFT titer[c] | |
|---|---|---|---|---|
| Serum | 1:2 | 1:10 | *B. equi* | *B. caballi* |
| 230 | 1.374, 1.362 | 1.560, 1.528 | Negative | 1:5 |
| 231 | 0.356, 0.356 | 0.439, 0.426 | 1:40 | 1:5 |
| 232 | 0.219, 0.254 | 0.334, 0.313 | 1:5 | Negative |
| 233 | 0.246, 0.260 | 0.351, 0.389 | 1:5 | 1:10 |
| 234 | 0.521, 0.486 | 0.761, 0.736 | 1:10 | Negative |
| 235 | 0.189, 0.198 | 0.314, 0.383 | 1:40 | 1:10 |
| 236 | 1.380, 1.351 | 1.535, 1.384 | Negative | 1:40 |
| 237 | 0.347, 0.277 | 0.465, 0.345 | 1:5 | 1:40 |
| 238 | 0.314, 0.308 | 0.461, 0.470 | * | * |
| H5 | 0.293, 0.303 | ND[d] | Negative | Negative |

[a]CI ELISA and CFT were performed as described in the text.
[b]Serum samples reducing mean of duplicate OD values to less than 3 SD below mean of control horses (<1.17) were considered positive. OD for control horses at a 1:2 dilution on this test day = 1.47 ± 0.10 (SD) (n = 9). OD for isotype control MAb = 0.145, 0.142.
[c]CFT titers are presented at the highest dilution yielding a positive result.
*, serum sample which reacted with CFT erythrocyte control antigen.
[d]ND, not done.

Of the 154 serum samples testable by CFT, 126 were both CFT and CI ELISA positive [CFT(+) CI ELISA(+)] for antibody to *B. equi*. Eighteen serum samples were negative in both tests, and CFT and CI ELISA results differed in the remaining 10 serum samples. Sixteen of the 18 serum samples negative by both the CFT and CI ELISA for antibody to *B. equi* were CFT(+) for *B. caballi*.

The ten serum samples in which the CI ELISA and CFT results differed were retested in both assays and analyzed by immunoprecipitation. CI ELISA, CFT, and immunoprecipitation results for the 10 discrepant serum samples are summarized in Table 3. Upon retesting, four of the CFT(+) CI ELISA(−) serum samples had decreased CFT titers. Two of these serum samples which were originally CFT(+) were negative in the repeat CFT. The decreasing CFT titers of these serum samples may reflect, at least in part, multiple freeze-thaw cycles.

TABLE III

CI ELISA, CFT, and immunoprecipitation results of sera differing on initial testing[a]

| | CFT | | CI ELISA | | Immunopre- |
|---|---|---|---|---|---|
| Serum | Original | Repeat | Original | Repeat | cipitation |
| 8 | Negative | Negative | Positive | Positive | Positive |
| 17 | Negative | Negative | Positive | Positive | Positive |
| 113 | Negative | Negative | Positive | Positive | Positive |
| 175 | Negative | Negative | Positive | Positive | Positive |
| H5 | Negative | Negative | Positive | Positive | Positive |
| 18 | 1:10 | Trace | Negative | Negative | Inconclusive |
| 22 | 1:10 | 1:5 | Negative | Negative | Inconclusive |
| 126 | 1:5 | Negative | Negative | Negative | Inconclusive |
| 167 | 1:40 | 1:40 | Negative | Negative | Inconclusive |
| 171 | 1:5 | Negative | Negative | Negative | Inconclusive |

[a]CI ELISA, CFT, and immunoprecipitation results were determined as described in the text. Serum samples which differed in the CI ELISA and CFT at original testing were retested by CI ELISA, CFT, and immunoprecipitation. CFT titers are presented as the highest dilution yielding a positive result.

Figure 5:
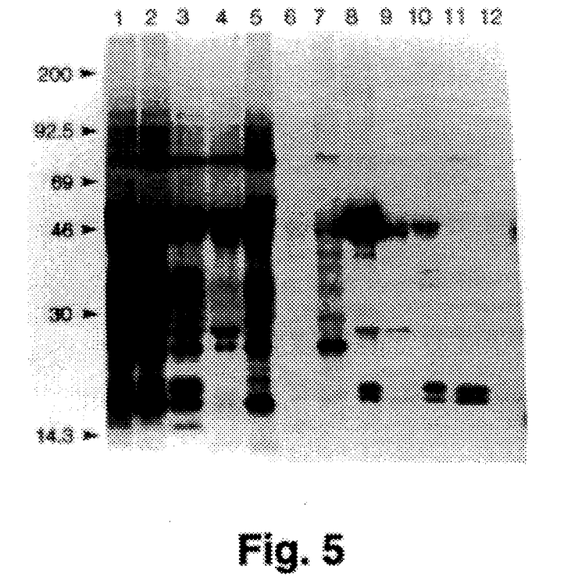
FIG. 5. Immunoprecipitation of [$^{35}$S]methionine-labeled in vitro translation products with 1:10 dilutions of sera yielding discrepant results in the CFT and CI ELISA. Lanes 1 to 5 represent sera which tested CFT(−) and CI ELISA(+), HS, 8, 17, 113, and 175, respectively. Lane 6, SN76N8401, CFT(−) control serum. Lanes 7 to 11 represent sera which tested CFT(+) and CI ELISA(−), 18, 22, 126, 167, and 171, respectively. Lane 12, serum 236, CFT(−) and CI ELISA(−). Numbers on left show size in kilodaltons.

Serum samples at a 1:10 dilution were evaluated for their ability to immunoprecipitate $^{35}$S-labeled in vitro translation products of *B. equi* merozoite mRNA as described by Knowles et al. (*Infect. Immun.* 59:2412–2417; 1991). FIG. 5 displays immunoprecipitation data from the five serum samples which were CFT(−) CI ELISA(+), the five serum samples which were CFT(+) CI ELISA(−), and two serum samples which were negative in both tests. Five serum samples which were CI ELISA(+) CFT(−) clearly immunoprecipitated multiple *B. equi* proteins that comigrated with proteins immunoprecipitated by positive control serum H5 (FIG. 5, lanes 1 to 5). Interestingly, serum H5, from a horse experimentally infected with *B. equi* and used as positive reference serum in the CI ELISA and immunoprecipitations, was one of the serum samples consistently negative by the CFT.

While *B. equi*-specific IgG(T) antibody was not measured in the five CI ELISA(+) CFT(−) serum samples, IgG(T) remains a likely explanation for the false-negative CFT results. It has been previously shown that IgG(T) specific for equine infectious anemia virus inhibits the CFT for detecting antibody to equine infectious anemia virus because IgG(T) does not fix complement by the classical pathway disclosed by McGuire et al. (*J. Immunol.* 107:1738–1744; 1971).

Immunoprecipitation results with the five serum samples which were GI ELISA(−) CFT(+) were inconclusive (FIG. 5, lanes 7 to 11). Fewer proteins were immunoprecipitated by these serum samples than by H5 serum. However, proteins not present in the negative control serum samples (FIG. 5, lanes 6 and 12) were immunoprecipitated by the CI ELISA(−) CFT(+) serum samples. The results obtained from the five CI ELISA(−) CFT(+) serum samples may represent false-positive GFT results; however, the immunoprecipitation results show reactivity with *B. equi* merozoite proteins (FIG. 5, lanes 7 to 11). Three of these serum samples (22, 126, 171) also had CFT titers to *B. caballi*, and t immunoprecipitation results with these serum samples may reflect serological cross-reactivity between *B. equi* and *B. caballi* merozoite proteins as previously recognized by Frerichs et al. (*Am. J. Vet. Res.* 30:697–702; 1969).

If the five CI ELISA(−) CFT(+) serum samples are true positives, there are at least three possible explanations: (i) a genetic inability of those horses to produce antibody to the epitope defined by MAb 36/133.97; (ii) absence of the epitope on *B. equi* isolates which infected those horses; and (iii) insufficient CI ELISA sensitivity. The third explanation does not seem likely since 32 of the CFT(+) CI ELISA(−) serum samples had CFT titers of only 1:5.

Figure 6:
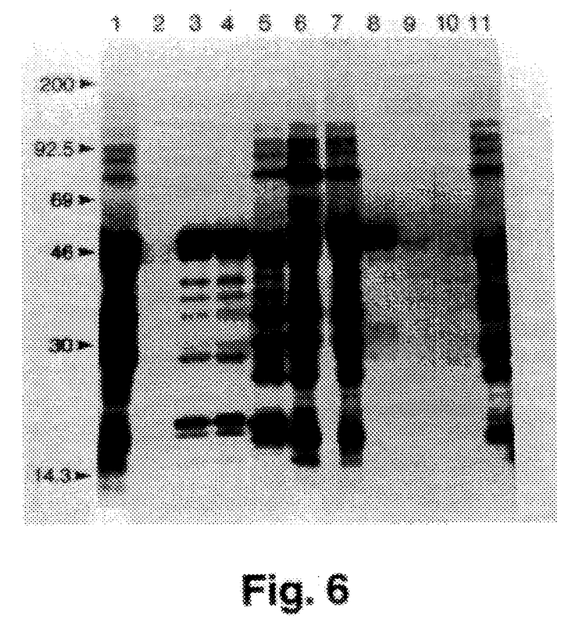
FIG. 6. Immunoprecipitation of [$^{35}$S]methionine-labeled in vitro translation products with 1:10 dilutions of equine sera with anticomplement activity or reactivity with CFT erythrocyte control antigen. Lanes: 1, serum H5; 2, serum 2, CFT(−) CI ELISA(−); 3 to 6, sera 215, 216,140, and 146, respectively, CFT (+) CI ELISA(+); 7, serum 213, anticomplement, CI ELISA(+); 8 and 9, sera 240 and 245, respectively, anticomplement, CI ELISA(−); 10, SN76N8401, CFT(−) control serum; 11, serum 238, reactive with CFT erythrocyte control, CI ELISA(+). Numbers on left show size in kilodaltons.
Figure 7:
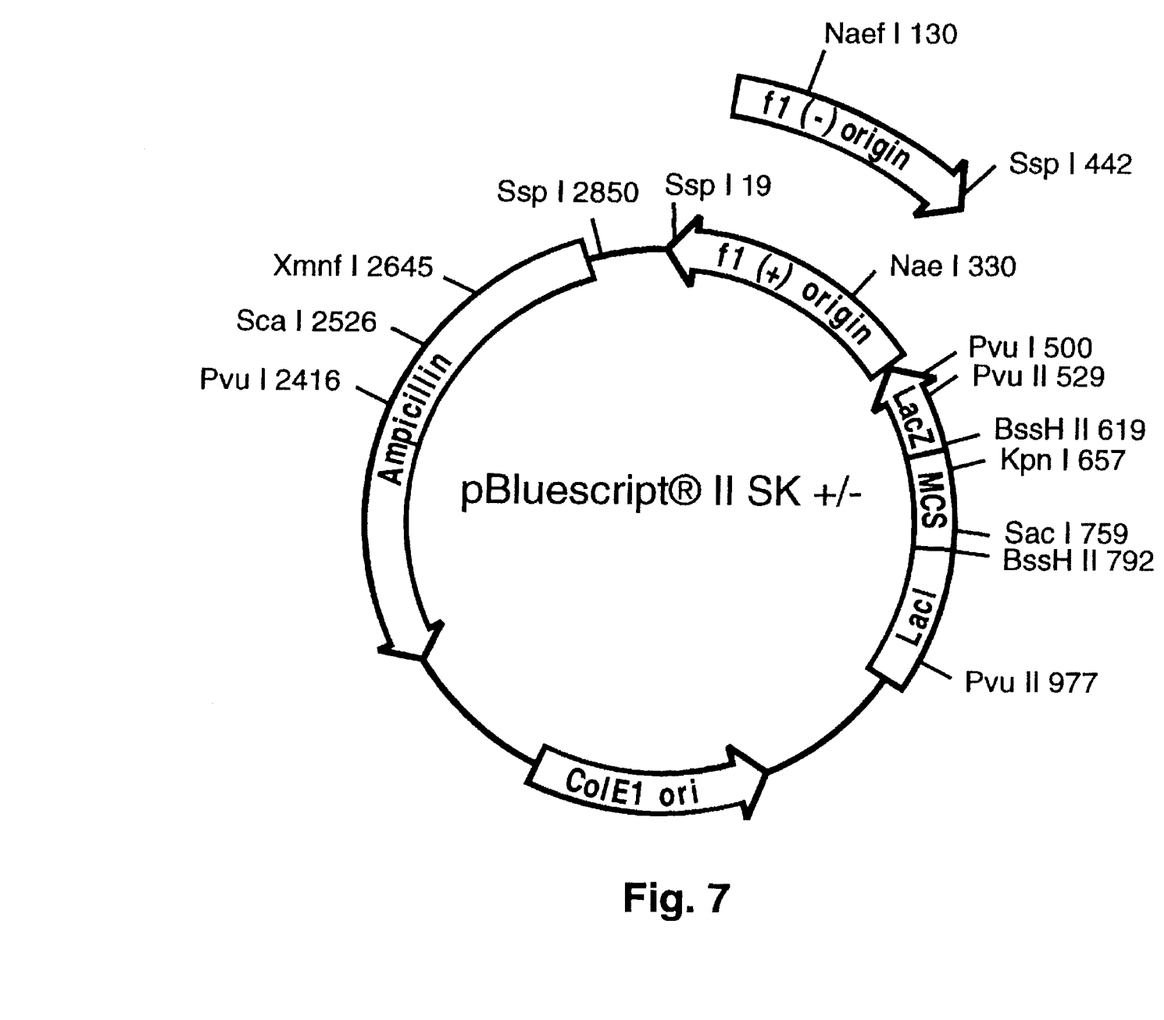
FIG. 7. Is the plasmid pBluescript™II SK(+/−)phagemid.

Three anticomplement serum samples and one serum sample which reacted with the CFT erythrocyte control antigen were tested by the CI ELISA and immunoprecipitation are shown in FIG. 6. Immunoprecipitations with these serum samples were compared with immunoprecipitations with H5 serum, four randomly selected CI ELISA(+) CFT (+) serum samples, and two serum samples negative by both tests (FIG. 2). One of three anticomplement serum samples and the serum sample reactive with CFT erythrocyte control antigen were positive by both CI ELISA and immunoprecipitation (FIG. 6, lanes 7 and 11). Two anticomplement serum samples were CI ELISA(−), and one of these serum samples was clearly negative by immunoprecipitation (FIG. 6, lane 9). Lane 8 of FIG. 6 represents immunoprecipitation with the additional anticomplement serum which was CI ELISA(−). Data obtained from this immunoprecipitation were inconclusive. The proteins in lane 8 not found in the control serum samples (lanes 2 and 10) may signify cross-reactivity between antigens of *B. equi* and *B. caballi*. Also, this serum may represent a false CI ELISA(−).

The collective data of this report indicate a high (94%) concordance between the CI ELISA and CFT for detecting antibody to *B. equi*. Since 16 of 18 serum samples in this study which were CI ELISA(−) CFT(−) for antibody to *B. equi* were CFT(+) for antibody to *B. caballi*, the CI ELISA is clearly specific for *B. equi*. Furthermore, the formatting of the CI ELISA overcomes the aforementioned limitations associated with the CFT, and as the data clearly indicate, the geographic conservation of the epitope recognized by MAb 36/133.97 allows reliable use of the CI ELISA to detect *B. equi* antibody in sera from horses worldwide.

EXAMPLE XVI

Construction and expression of cDNA library

*B. equi* merozoite mRNA was isolated from infected erythrocytes as previously described in Example II. cDNA library construction was performed utilizing the methods of Maniatis et al. (1982. *Molecular Cloning: A Laboratory Manual.* Cold Spring Harbor Laboratory, Cold Spring Harbor, N.Y.). In this process 2 µg of merozoite mRNA were copied by reverse transcriptase followed by T4 polymerase (pharmacia). The resultant DNA was blunted, EcoRI linkers were applied and ligation into the EcoRI-site of LAMBDA ZAPII® (Stratagene Cloning Systems) was carried out. The lambda library in *E. coli* XL-blue was screened with MAb 36/133.97 by immunoblot assay. Transfer of bacteria to nitrocellulose was done by standard procedures and recombinant protein was detected using MAb 36/133.97 (2 µg/ml), rabbit anti-mouse second antibody and $^{125}$I protein A. Positive plaques were isolated, replated and rescreened to achieve purity. Recombinant plasmids were excised from the bacteriophages and following induction with 5 mM isopropyl-1-B-D-thiogalactopyranoside (IPTG), tested for expression by immunoblot assay.

EXAMPLE XVII

Plasmid purification via cesium chloride

The bacterial suspension containing pBluescript/10E3; which has been deposited under the Budapest Treaty in the American Type Culture Collection (12301 Parklawn Drive, Rockville, Md., 20852, USA) on Jan. 10, 1995, and has been assigned Deposit Number ATCC 97016; was transferred to 250 ml proplyene bottles and pelletized by centrifugation in a Beckman at 7000 rpm for 20 min at 4° C. As a separate step 37.5 mg of lysozyme was dissolved in 7.5 ml of an aqueous reagent solution comprising 50 mM glucose, 25 mMTris and an HCl adjusted pH of 8.0 (Solution A). The pelleted bacteria are then suspended in the lysozyme-containing Solution A and transferred to a 50 ml polypropylene centrifuge tube. The suspension was allowed to stand at room temperature for 5 min, at which point 15 ml of an aqueous reagent solution comprising 0.2 N NaOH and 1% SDS (Solution B) was added and thoroughly mixed. The tube was then incubated on ice for 10 min before adding 11 ml of an aqueous reagent solution composed of 60 ml of 5 M potassium acetate, 11.5 ml of glacial acetic acid and 22.5 ml of distilled water (Solution C), and thoroughly mixed. The contents of the tube were then centrifuged at 17,000 rpm for 40 min at 4° C. in a polyallomer SW28 centrifuge tube. The resultant liquid phase of 32 ml was then distributed evenly between two SW28 tubes. The plasmid DNA present in the tubes was then precipitated by the addition of 9.6 ml of isopropanol to each tube and being allowed to stand at room temperature for 20 min. The plasmid DNA was then pelleted by centrifugation at 12,000 rpm for 30 min at 4° C. The pellets were then lyophilized, combined and suspended in precisely 4.3 ml of TE Buffer (pH 8.0) in a SW28 tube. 4.63 grams of CsCl was added to the sample. After equilibration at room temperature 80 µl of Ethictrium Bromide (10 mg/ml) was added and mixed thoroughly. The sample was then placed in a Ti65 polyallomer tube and heat-sealed. The tube was then centrifuged with a Vti65 rotor at 48,000 rpm for 16 hours at 20° C. After centrifugation, the plasmid band was then extracted by syringe as part of a 1.2 ml sample and expelled into a polyallomer SW41 centrifuge tube. The DNA was then precipitated by the addition of 2.4 ml of water and 7.2 ml of 95% ethanol to the 1.2 ml sample. The sample was then stored at −20° C. for one hour and then centrifuged with a SW41 rotor at 15,000 rpm for 30 min at 4° C. The pellet was then lyophilized and transferred to a 1.5 ml microcentrifuge tube where it was solubilized in approximately 300 µl of TE Buffer (pH 7.2). Approximately 30 µl of RNAse A Solution was added to the sample which was then incubated at 37° C. for 30 min. Approximately 2 µg of Proteinase K was then added to the sample which was then incubated again at 37° C. for 30 min. The sample was then extracted with phenol/chloroform. A reextraction with phenol/chloroform was then performed using 200 µl of TE Buffer (pH 7.2). The sample was then extracted with water-saturated ether. After removal of the ether phase the sample was precipitated by adding 1/10 th volume of 5 M NaCl and 3 volumes of the combined sample plus salt of 95% ethanol. The sample was then stored at −20° C.

EXAMPLE XVIII

Banahan Std. high frequency transformation

A sample of DH5 bacteria (from BRL Product Profile-see Hanahan, D., 1983, *J. Mol. Biol.* 166:557–580) was streaked onto SOB(Mg++)+ agar and incubated at 37° C. for about 18 hours. The colonies were transferred into 1 ml SOB broth per colony. Each 1 ml cell suspension was used to inoculate a flask containing 10 ml of SOB broth. The flasks were incubated at 37° C. and 250 rpm until a cell density of at least 4×10⁷ viable cells/ml was reached. The cell suspension was then cooled on ice for 10–15 min. The suspension was then centrifuged at 2000 rpm for 12 min at 4° C. to pelletize the cells. The cells were then resuspended in 3.3 ml of TFB and incubated on ice for 10 min. The cells were then repelletized by centrifugation at 2000 rpm, for 12 min at 4° C. The cells were then resuspended in 0.8 ml of SOB with TFB, adding 28 µl of DMSO and DTT to make a 3.5% concentration. The sample was then incubated on ice for 10 min and a second 28 µl portion of DMSO and DTT was added to make a final concentration of 7%. The sample was then incubated on ice for 10 min. 210 µl of the cell suspension was then combined with less than 20 µl of the DNA solution (plasmid) resulting from Example XVII and incubated on ice for 20 min. The reaction was then heat shocked in a 42° C. water bath for 90 seconds and immediately chilled on ice for 2 min. 800 µl of SOC broth was then added to the sample and allowed to incubate at 37° C. for 30 min. 500 µl of the reactant was then spread on a YT/Amp++ plate and allowed to dry before incubation at 37° C.

| +S.O.C./S.O.B. Preparation | | | |
|---|---|---|---|
| Reagent | Conc. | Amt./ 100 ml | 485H₂O/ 500 ml |
| BactoTryptone | 2.0% | 2.0 gm | 10 gm |
| Yeast Extract | 0.5% | 0.5 gm | 2.5 gm |
| NaCl | 10 mM | 1.0 ml 1M NaCl | 5.0 ml |
| KCl | 2.5 mM | 0.25 ml 1M KCl | 1.25 m. |
| MgCl2.MgSO4 | 20 mM | 1.0 ml 2M Mg Stock (10 mM each) | 5.0 ml |
| Glucose | 20 mM | 1.0 ml 2M Glucose | 5.0 ml |
| Distilled H₂O | | qs to 100 ml total volume | |

S.O. Broth

Bactotryptone, yeast extract, NaCl and KCl were added to 97 ml of distilled water, dissolved and then autoclaved. MgCl₂ and MgSO₄ were then added at a rate of 1/100 to the solution.

S.O.B. Plates

Same procedure for S.O. broth but with the additional inclusion of agar to the solution at a rate of 15 g/l prior to autoclaving.

S.O.C. Broth

Same procedure for S.O. broth but with the additional inclusion of 2M glucose at a rate of 1/100 after autoclaving.

| ++YT/Amp Plate Agar | | | |
|---|---|---|---|
| Reagent | 1 liter | 500 ml | 250 ml |
| NaCl | 5.0 gm | 2.5 gm | 1.25 gm |
| Bacto Yeast Extract | 5.0 gm | 2.5 gm | 1.25 gm |
| Bacto Tryptone | 8.0 gm | 4.0 gm | 3.0 gm |
| Bacto Agar | 15 gm | 7.5 gm | 3.75 gm |

The first three ingredients are dissolved in the desired volume of distilled water. The agar is then suspended and autoclaved for 20–30 min.

After the agar has cooled to about 50° C., 50 mg/L of ampicillin are added to the agar Just before it is poured into the plates.

EXAMPLE XIX

Production of recombinant antigen

The purified and isolated plasmid pBluescrtpt/lOE3 resulting from the cesium chloride purification process of Example XVI (see Maniatis et al., 1982. *Molecular Cloning: A Laboratory Manual.* Cold Spring Harbor Laboratory, Cold Spring Harbor, N.Y.; herein incorporated by reference) was used in an amount of 1 µg to transform *E. coli* strain DH 5 (Bethesda Research Laboratories) using the Hanahan Standard High Frequency Transformation of Example XVIII (see Hanahan, D., 1983, *J. Mol. Biol.* 166:557–580; herein incorporated by reference). The entire transformation reaction was added to 250 ml of YT broth containing 12.5 mg ampicillin and 59.5 mg IPTG. The culture was incubated overnight at 37° C. and 250 rpm. The cells from the culture were then pelletized by centrifugation at 1000×g for 10 min at 4° C. The resultant pellet was then resuspended in 40 ml of Proteinase Inhibition Buffer+ and recentrifuged at 1000×g for 10 min at 4° C. The resultant pellet was then resuspended in 20 ml of Proteinase Inhibition Buffer containing 1 mg/ml lysozyme and incubated on ice for 20 min. NP40 (Sigma Chemicals, #N3516) was added to 1% (200 µl) was added, and the solution was incubated on ice for 10 min. The solution was then sonicated twice at 100 watts with the probe in the solution; with each event lasting 20 min and pausing 15 min on ice between the two events. The solution was then centrifuged at 12,000×g for 10 min at 4° C. The supernatant, representing the recombinant antigen, was then recovered and stored at 4° C.

| †Proteinase Inhibitor Buffer | | |
|---|---|---|
| | 100 ml | 500 ml |
| 50 mM Tris ph 8.0 | 606 mg | 3.03 gm |
| 5 mM EDTA | 186 mg | 0.93 gm |
| 5 mM Iodoacetamide | 92.5 mg | 0.46 gm |
| 0.1 Mm TLCK | 3.69 mg | 18.45 gm |
| 1 mM PMSF | 2.27 ml | 11.35 ml |

EXAMPLE XX

Coating a plate with recombinant antigen

The recombinant antigen of Example XIX was slowly vortexed then made into a 1:10 dilution by addition of 50 μl of antigen to 450 μl of coating buffer†. Two tubes of 1:100 dilution were then prepared by adding 50 μl of the 1:10 dilution to 450 μl of the coating buffer. The coating buffer was then added to the wells of a Dynatech Immulon 2 plate, skipping columns 1 and 12—the total volume of the coating buffer being added equaling 100 ml less the volume of the diluted antigen. The appropriate amount of the 1:100 dilution was then added to the coating buffer in each well. The plate was sealed and stored at room temperature overnight.

| †Coating Buffer | | |
|---|---|---|
| To make 100 ml: | Add to 75 ml d H$_2$O: | |
| | 0.88 gm | NaCl |
| | 0.02 gm | KCl |
| | 0.158 gm | Na$_2$HPO$_4$ |
| | 0.02 gm | KH$_2$PO$_4$ |
| | Mix and adjust pH to 7.4 with 1M HCl | |
| | 0.446 gm | MgCl$_2$.6H$_2$O |
| | Add H$_2$O to bring volume to 100 ml | |

We claim:

1. An isolated and purified merozoite protein of *Babesia equi* containing a conserved epitope specifically bound by Mab 36/133.97, ATCC 11788 that is useful as an indicator of infection by *Babesia equi* in horses.

2. The protein of claim 1 having an amino acid sequence of SEQ ID NO:1
RPPVKMISKS FAFVFASIAI SSILAEEEKP KASGAWDFQ LESIDHVTID 51 KQSEEHIVYT AHEGYAVEKV KEGDSVIKTF DLKEQTPKTV VRHIKDNKPY 101 WIAVESALH LVLKKDGDKW VELEVAEFYQ EVLFKGFEAV SVDiAAAVSD 151 KFTETTFGSG KKHTFKAPGK RVLKVVDGKT ELIDGDNEVV LDLELFVSSD 201 NKVARVVYLY KGDGRIKEIF LKLVEKAWKRVEVKDAAETL HGINSTFPAD 251 YKWYDGFSV YGALLAVAAI AFSTLFY 277.

3. The protein of claim 1 derived by recombinant means.

4. A vector comprising cDNA which encodes for the protein of claim 2.

5. The vector of claim 4 wherein said vector is a plasmid.

6. The vector of claim 5 wherein said plasmid is ATCC 97016.

7. A cell containing the vector of claim 4.

8. The cell of claim 7 wherein said cell is *E. coli*.

9. An antibody which is specifically binds the protein of claim 1.

10. The antibody of claim 9 wherein said antibody is monoclonal.

11. A hybridoma which produces the monoclonal antibody of claim 10.

12. An immunoassay method for determining antibodies to *Babesia equi* in horses comprising, as indication of infection, the steps of:

A) collecting serum from a horse to be tested;

B) contacting the serum with antigen containing a conserved epitope of a merozoite protein of *Babesia equi* wherein said conserved epitope is specifically bound by Mab 36/133.97, ATCC HB 11788; and C) detecting the presence of the antigen-antibody complex.

13. The method of claim 12 wherein the immunoassay is competitive.

14. The method of claim 13 wherein the immunoassay utilizes a monoclonal antibody.

15. The method of claim 12 wherein a recombinant antigen is utilized.

* * * * *

UNITED STATES PATENT AND TRADEMARK OFFICE
CERTIFICATE OF CORRECTION

PATENT NO. : 5,643,737
DATED : July 1, 1997
INVENTOR(S) : Donald P. Knowles, Jr.; Lance E. Perryman It is certified that error appears in the above-identified patent and that said Letters Patent is hereby corrected as shown below:

Claim 1, line 3; after "ATCC" insert --HB--

Signed and Sealed this

Sixth Day of January, 1998

*Attest:*

BRUCE LEHMAN

*Attesting Officer*    Commissioner of Patents and Trademarks